United States Patent
Anderson et al.

(10) Patent No.: US 7,250,047 B2
(45) Date of Patent: Jul. 31, 2007

(54) SYSTEM AND METHOD FOR TREATING TISSUE

(75) Inventors: Robert S. Anderson, Livermore, CA (US); Steven Randal Young, Discovery Bay, CA (US); Yoni Iger, Haifa (IL)

(73) Assignee: Lumenis Ltd., Yokneam (IL)

( * ) Notice: Subject to any disclaimer, the term of this patent is extended or adjusted under 35 U.S.C. 154(b) by 143 days.

(21) Appl. No.: 10/767,459

(22) Filed: Jan. 30, 2004
(Under 37 CFR 1.47)

(65) Prior Publication Data

US 2005/0049543 A1 Mar. 3, 2005

Related U.S. Application Data

(63) Continuation-in-part of application No. 10/743,308, filed on Dec. 23, 2003, now abandoned, and a continuation-in-part of application No. 10/642,037, filed on Aug. 15, 2003, now abandoned.

(60) Provisional application No. 60/472,704, filed on May 21, 2003, provisional application No. 60/444,107, filed on Jan. 31, 2003, provisional application No. 60/436,334, filed on Dec. 23, 2002, provisional application No. 60/436,327, filed on Dec. 23, 2002, provisional application No. 60/403,973, filed on Aug. 16, 2002.

(51) Int. Cl.
*A61B 18/18* (2006.01)
*A61N 5/00* (2006.01)

(52) U.S. Cl. .................. 606/32; 128/898; 607/88

(58) Field of Classification Search .......... 128/898; 606/9, 41; 607/88–94
See application file for complete search history.

(56) References Cited

U.S. PATENT DOCUMENTS

| | | | |
|---|---|---|---|
| 4,742,235 A | 5/1988 | Koji | |
| 5,630,811 A | 5/1997 | Miller | |
| 5,735,844 A | 4/1998 | Anderson et al. | |
| 5,772,597 A * | 6/1998 | Goldberger et al. | 600/473 |
| 5,853,407 A | 12/1998 | Miller | |
| 5,948,011 A * | 9/1999 | Knowlton | 607/101 |
| 6,050,993 A * | 4/2000 | Tu et al. | 606/41 |
| 6,071,239 A | 6/2000 | Cribbs et al. | |
| 6,162,220 A * | 12/2000 | Nezhat | 606/48 |
| 6,169,926 B1 * | 1/2001 | Baker | 607/99 |
| 6,187,001 B1 | 2/2001 | Azar et al. | |
| 6,210,402 B1 | 4/2001 | Olsen et al. | |
| 6,273,884 B1 | 8/2001 | Altshuler et al. | |

(Continued)

OTHER PUBLICATIONS

International Search Report for PCT/IL04/00846 mailed Sep. 26, 2005.

*Primary Examiner*—Henry M. Johnson, III
(74) *Attorney, Agent, or Firm*—Pearl Cohen Zedek Latzer, LLP

(57) ABSTRACT

A method, device, and system for modifying or destroying selected tissue, by selecting an area of tissue for treatment, collecting the area between a plurality of energy transmitting elements, applying an electric current and/or electromagnetic radiation between the energy transmitting elements, and applying the electric current and/or electromagnetic radiation until, for example, the cells are modified or destroyed. Cooling may be applied to prevent unwanted modification. Conducting mediums may be applied to control tissue modification. Embodiments of the present invention may be used for treatment of fat cells, acne, lesions, tattoo removals etc.

18 Claims, 8 Drawing Sheets

U.S. PATENT DOCUMENTS

| | | |
|---|---|---|
| 6,387,380 B1 | 5/2002 | Knowlton |
| 6,419,672 B1 * | 7/2002 | Utsugi ............................ 606/9 |
| 6,438,424 B1 | 8/2002 | Knowlton |
| 6,461,354 B1 | 10/2002 | Olsen et al. |
| 6,508,813 B1 | 1/2003 | Altshuler |
| 6,511,475 B1 | 1/2003 | Altshuler et al. |
| 6,514,250 B1 | 2/2003 | Jahns et al. |
| 6,517,532 B1 | 2/2003 | Altshuler et al. |
| 6,595,934 B1 | 7/2003 | Hissong et al. |
| 6,605,080 B1 | 8/2003 | Altshuler et al. |
| 6,652,518 B2 * | 11/2003 | Wellman et al. ............... 606/41 |
| 6,662,054 B2 | 12/2003 | Kreindel et al. |
| 6,663,618 B2 * | 12/2003 | Weber et al. .................... 606/2 |
| 6,663,622 B1 * | 12/2003 | Foley et al. .................... 606/34 |
| 6,676,655 B2 * | 1/2004 | McDaniel ........................ 606/9 |
| 6,702,808 B1 | 3/2004 | Kreindel |
| 6,719,754 B2 | 4/2004 | Underwood et al. |
| 6,749,624 B2 | 6/2004 | Knowlton |
| 6,766,202 B2 | 7/2004 | Underwood et al. |
| 6,800,122 B2 | 10/2004 | Anderson et al. |
| 6,849,075 B2 * | 2/2005 | Bertolero et al. .............. 606/41 |
| 6,916,316 B2 * | 7/2005 | Jay ................................. 606/9 |
| 2002/0133152 A1 * | 9/2002 | Strul ............................ 606/50 |
| 2002/0143326 A1 * | 10/2002 | Foley et al. ................... 606/41 |
| 2003/0028186 A1 | 2/2003 | Kreindel |
| 2005/0215887 A1 | 9/2005 | Slatkine |
| 2007/0010861 A1 * | 1/2007 | Anderson et al. .............. 607/96 |

* cited by examiner

SYSTEM AND METHOD FOR TREATING TISSUE

CROSS REFERENCE TO RELATED APPLICATIONS

This application claims priority from U.S. Provisional Patent Application No. 60/472,704, filed May 21, 2003, entitled "SYSTEM AND METHOD FOR ACNE REMOVAL USING LIGHT, SUCTION AND COOLING", which is incorporated in its entirety herein by reference, and from U.S. Provisional Patent Application No. 60/444,107, filed Jan. 31, 2003, entitled "THERAPEUTIC TREATMENT MODALITY USING EPIDERMAL AND DERMAL STRETCHING", which is incorporated in its entirety herein by reference. This application is a Continuation In Part (CIP) of U.S. patent application Ser. No. 10/743,308, filed 23 Dec. 2003 now abandoned, entitled "SYSTEM AND METHOD FOR DESTROYING UNDESIRABLE TISSUE", which is incorporated in its entirety herein by reference, which in turn claims priority from U.S. Provisional Patent Application No. 60/436,327, filed Dec. 23, 2002, entitled "NON-INVASiVE SYSTEM AND METHOD FOR REMOVAL OF ADIPOSE TISSUE", and from U.S. Provisional Patent Application No. 60/436,334, filed Dec. 23, 2002, entitled "METHOD FOR DESTROYING UNDESIRABLE TISSUE". This application is also a Continuation In Part (CIP) of U.S. patent application Ser. No. 10/642,037, filed 15 Aug. 2003 now abandoned, entitled "METHOD FOR DESTROYING UNDESIRABLE TISSUE", which in turn claims priority from U.S. Provisional Patent Application No. 60/403,973, filed on Aug. 16, 2002 and entitled "Method of Destroying Undesirable Tissue", which are incorporated entirety herein by reference.

FIELD OF THE INVENTION

The present invention relates to methods and devices useful in modification, treatment, destruction, or removal of tissue.

BACKGROUND OF THE INVENTION

There are both physical and psychological reasons for treating and/or destroying undesirable tissue, for example, by destroying excess cells (e.g., fat cells, acne, tattoo ink, wrinkles, lesions, etc.), stimulating, destroying or otherwise modifying tissue, etc. The physical reasons may include prevention of heart disease, stroke, and diabetes, for example, by removal fatty cells. The psychological reasons may include improvement of self-image, which may accompany treatments that may reduce or modify excess tissue. Removing or otherwise modifying excess undesirable tissue has started playing an important role in medical and cosmetic procedures.

For example, adipose tissue, or "fat", is primarily located in the hypodermis, but may be found in other areas. The hypodermis is a layer of subcutaneous tissue located beneath the dermis. The cells are large compared to other cells in the outer layers of the body. They are generally round in shape, but may also be polyhedral when pressed together to form a "layer of fat". The nucleus of adipose cells is located near the cell membrane. Most of the volume of the cell is composed of a single droplet of liquid consisting of 90% triglycerides. There is little to no water inside a fat cell. Outside the fat cell is an area comprised of reticular fibers and a plexus of small capillaries. The capillaries transfer the triglycerides from the adipose cell to other cells when the body needs to generate energy.

One of the known methods of removing excess adipose or fat tissue is liposuction. This is an invasive procedure in which the fat is destroyed mechanically and then extracted using a suction device.

In the case of acne, the output duct of the sebaceous gland becomes blocked due to processes in the dermis and epidermis. The lipids that are secreted by the sebaceous gland begin to accumulate. Also located in the sebaceous glands are P.Acnes bacteria. These thrive on the accumulated lipids and their population begins to grow. This triggers a response from the immune system as it tries to control the population of P.Acnes, resulting in acne inflammation.

The P.Acne bacteria contain porphyrins. The two major porphyrins found in the P.Acne bacteria are coproporphyrin and uroporphyrin. Both are measured in urine analysis too determine liver and kidney problems. The peak absorption for coproporphyrin is 402 to 403 nm and for uroporphyrin the peak absorption is at 406 to 407 nm. Recent studies have indicated that a third porphyrin called protoporphrin is also present, which has a primary absorption point at 430 mm Some current therapies use drugs to control the events in the dermis and epidermis that lead to the blocking of the sebaceous gland. Other therapies try to lower the immune systems response to the P.Acne bacteria. Still others try to destroy the P.Acne bacteria, for example, by applying blue light at approximately 400 nm to destroy the P.Acnes bacteria. Blue light is a relatively high frequency energy with a relative low penetration ability, therefore substantial amounts of blue light may need to be transmitted.

It would be highly advantageous to have a non-invasive method for destroying or modifying tissue, which is relatively easy, efficacious, and cost effective to apply.

SUMMARY OF TE INVENTION

Embodiments of the present invention relate to apparatuses, systems, and methods of treating human/animal tissue, for example by isolating or selecting areas of tissue and transmitting electrical current and/or electromagnetic radiation using energy transmitting elements. Electromagnetic radiation may include, for example, therapeutic ultrasonic waves, therapeutic light treatment, therapeutic radio frequency (RF) treatment, etc.

According to some embodiments of the present invention selected areas of tissue may be cooled to help prevent modification of these areas, while other areas that have not been cooled may be more readily modified. Some embodiments may include cooling the epidermis. Other embodiments may include cooling the dermis.

According to some embodiments of the present invention a conductive medium may be applied to the epidermis to increase conductivity in the epidermis, thereby helping prevent modification of the epidermis.

In other embodiments a method is provided for destroying adipose tissue in the hypodermis of a human subject, by selecting an area of tissue for treatment, collecting the selected area, applying an electric current and/or electromagnetic radiation using an energy transmitting element, and applying the electric current and/or electromagnetic radiation until the temperature of the adipose cells within the tissue reaches a level at which the adipose cells are destroyed. Two or more energy transmitting elements may be used.

According to some embodiments of the present invention, current supplied by an energy source may be AC current or DC current. Some embodiments of the present invention may include applying current in pulses and/or continuously.

In other embodiments a method is provided for destroying blood vessels in tissue that comprise port wine stains, rosacea, telangiectasias, and other vascular lesions.

In a further embodiment acne may be removed by using blue light. In some embodiments cooling may be used to prevent or minimize damage to the epidermis or dermis when applying blue light. In some embodiments Ultraviolet B (UVB) and Ultraviolet A (UVA) may be applied to collected skin areas to destroy P.Acnes bacteria.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1A:
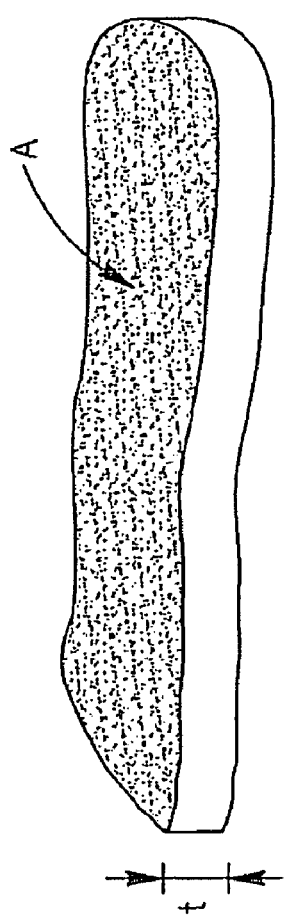
FIGS. 1A and 1B are schematic illustrations of a mass of tissue indicating the principle of conservation of volume, as applied according to embodiments of the present invention.

It will be appreciated that for simplicity and clarity of illustration, elements shown in the drawings have not necessarily been drawn to scale. For example, the dimensions of some of the elements may be exaggerated relative to other elements for clarity. Further, where considered appropriate, reference numerals may be repeated among the drawings to indicate corresponding or analogous elements throughout the serial views.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

In the following detailed description, numerous specific details are set forth in order to provide a thorough understanding of the present invention. However, it will be understood by those skilled in the art that the present invention may be practiced without these specific details.

The phrase "adipose tissue" as used herein may encompass, for example, "fat", degraded tissue, collagen, tumors, lesions, acne, tattoo ink, scars, or other undesirable tissue elements. Adipose tissue is used herein as an example of undesirable tissue, but it should be understood that embodiments of the present invention are applicable to other classes of tissue. The term "energy transmitting element" as used herein may encompass, for example, an energy conducting element, energy receiving element, energy generating element, energy controlling element etc. For example, an electrode, light guide, transceiver etc. may be an energy transmitting element.

The epidermis and the dermis skin layers of humans are complex organs. The majority of these organs comprise extra-cellular space, which is an intricate network of large molecules often referred to as the extra-cellular matrix. Connective tissues such as collagen, glycosaminoglycans (GAGs), and elastin are among the major components of the extra-cellular matrix that give the skin many of its characteristic features. Collagen, GAGs, and elastin may all be produced by cells called fibroblasts, also present in the dermis and epidermis. Additional substances including the specialized protein melanin, hair, and tattoo ink may be present as well. All of these elements are described in more detail below.

Collagen is a structural protein that consists of long, ropelike chains of connective tissue. These chains become organized into a variety of structures that can support relatively high tension, so that collagen plays an important role in giving the skin its tensile strength.

GAGs are sulfated oligosaccharide chains made up of repeating disaccharide units, and are routinely linked to glycoproteins. When associated with collagen, GAGs help to provide the skin with its compressibility.

Elastin is a structural protein comprising polypeptide chains that are cross-linked together to form rubberlike, elastic fibers. Each elastin molecule uncoils into a more extended conformation when the fibers are stretched, and will recoil spontaneously as soon as the stretching force is relaxed. Elastin is therefore a protein that provides the skin with elasticity.

Melanin is a protein that gives the skin its brownish color, and that can absorb many different types of energy and dissipate them in the form of heat. Melanin may therefore protect the skin from harmful ultraviolet radiation. However, melanin may also inhibit treatment in cases where it is desirable to apply radiation to the dermis or epidermis, as it tends to absorb the applied radiation and dissipate it. In fact, if the energy input is too great, this dissipation can be expressed in the form of activated chemical species that can damage cellular macromolecules, resulting in cell death, mutations, and even cancer. This may be the primary connection between overexposure to sunlight (i.e., a sunburn) and skin cancer.

Hair is a complex structure located in the epidermis. It grows from structures called papilla, which are generally located 2 to 4 mm beneath the surface of the skin. Like skin color, hair color is determined by the concentration of melanin it contains. The hair is relatively inelastic, as it is comprised mainly of hard keratin proteins, with relatively little elastin.

Tattoo ink varies widely in its composition, often including such elements as aluminum, oxygen, titanium, and carbon. After application of the ink, these elements reside in the extracellular matrix, often surrounded by fibrous tissues that may be generated by fibroblasts in response to the presence of the foreign substance.

While various types of tissues and conditions are discussed herein, other conditions and tissues may be treated using embodiments of the present invention.

According to some embodiments of the present invention the natural and/or foreign substances located in the epidermis or dermis may be treated by stimulating, modifying and/or removing one or more of these substances. For example, one or more of these substances may be modified to remove fat cells acne, tattoo ink etc. from the skin, or to remove unwanted hair from the skin, or stimulate hair growth in particular regions. These treatments may involve, for example, a noninvasive and focused application of ultrasonic vibrations or electromagnetic radiation to selected tissue.

In general, the depth of the target is very important when treating the dermis or epidermis with various surface treatments, including both ultrasonic waves and electromagnetic radiation. As the waves travel within the epidermis or dermis, they are attenuated by both scattering and absorption. The intensity of the waves may therefore decrease to an ineffective level by the time it reaches the depth of the target. In treatments involving radiation, for example, as described above, the presence of melanin between the surface of the skin and the treatment target may absorb a high proportion of the applied energy before it reaches its target, and then dissipating it as heat, thereby inhibiting effective treatment. One way to overcome this problem is to increase the intensity of the treatment at the surface of the skin, but this may generally be done only up to the level that might cause damage to the epidermis.

Embodiments of the present invention may use the principle of conservation of volume for an incompressible substance. For example, when a multi-dimensional substance is stretched along one direction, the substances may constrict along one or more of the remaining directions, provided that its volume remains constant. For example, when a rubber band is stretched, its thickness and width become smaller. When sheet metal is bent around a form, its thickness diminishes. When a balloon is inflated, the wall thickness of the balloon is decreased.

Figure 1B:
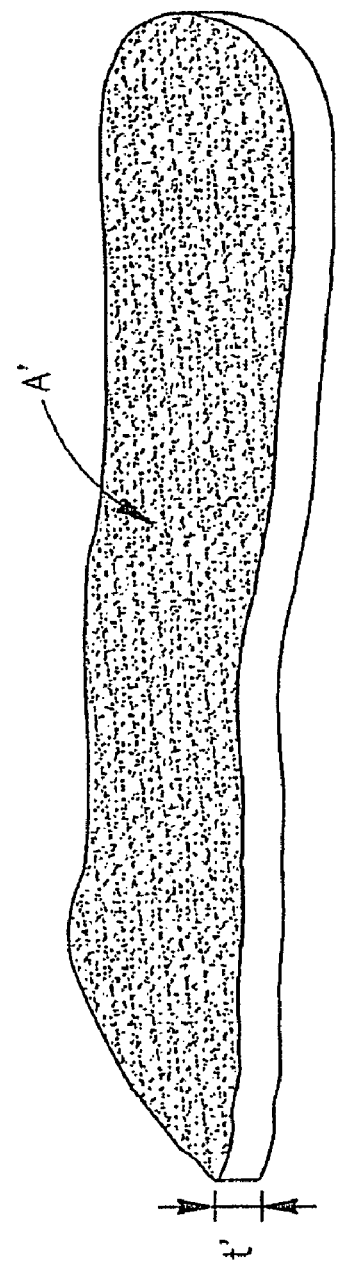

More specifically, consider a thin sheet of material with constant volume V, that has initial thickness t and surface area A, as shown in FIG. 1A. If the volume remains constant (or substantially so), but the substance is stretched so that its surface area increases (to A'), then the thickness decreases, for example to t' as shown in FIG. 1B. For a substance that is substantially incompressible, its density and volume remain constant, and the ratio of final to initial thickness is equal to the ratio of initial to final surface area:

$$V_{after} = V_{befroe}$$
$$A't' = At$$
$$\Rightarrow \frac{t'}{t} = \frac{A}{A'}$$

This shows that in the simple case of incompressible substances, increasing the surface area of the substance by any factor may lead to a decrease in its thickness by that same factor.

Relative to the known stretchable materials, human tissue is relatively elastic and may be easily stretched. Although not perfectly incompressible, the human epidermis and dermis substantially conform to the same principle as an incompressible substance. If the epidermis and the dermis are stretched, they become thinner. By becoming thinner, substances in the epidermis and or dermis such as the papilla move closer to the surface. Likewise, a deposit of tattoo ink, fat cells, P.Acnes bacteria etc. also move closer to the surface.

By stretching the skin, it is possible to decrease the distance between the skin's surface and a target location within the dermis or epidermis. This may have the effect of decreasing the attenuation of penetrating energies, such as electric current, ultrasound, or electromagnetic radiation, which might be applied to the skin during treatment.

The electrical resistance of various tissues in animals/humans varies among tissue types. For example the electrical resistance of bone is much higher than the electrical resistance of muscle. The electrical resistance of fat is much higher than the resistance of the dermis and epidermis. An element within the human body that plays a dominant role in electrical resistance is water. Tissue with high water content has low electrical resistance. Tissues with low water content such as bone and fat have high electrical resistance.

According to some embodiments of the present invention, an electric current may be conducted through various types of tissues, thereby increasing the temperature in elements of tissue with a higher resistance more than in elements of tissue with a lower resistance. It is well known that elevating the temperature of a tissue can modify the tissue, therefore using the difference in temperature of the various elements in tissues, modifications may be made to selected tissue elements without significantly affecting other tissue elements. Various embodiments of the present invention may have other and different effects, and may rely on other and different bases.

In the case of adipose tissue, for example fat tissue, the electrical resistance of such tissue may be, for example, 10 to 14 times higher than that of other tissues in the outer layer of the human body. The lack of water in adipose cells may cause high electrical resistance. For example, adipose cells may include 90% triglycerides and approximately 10% water. Other cells in the outer layer of the human body may generally contain 70% or more water and hence have a low electrical resistance. The cells of the stratum cornea, the outer most layer of the epidermis, also have a low water content and hence a higher electrical resistance. Other suitable water levels may be observed.

Figure 2:
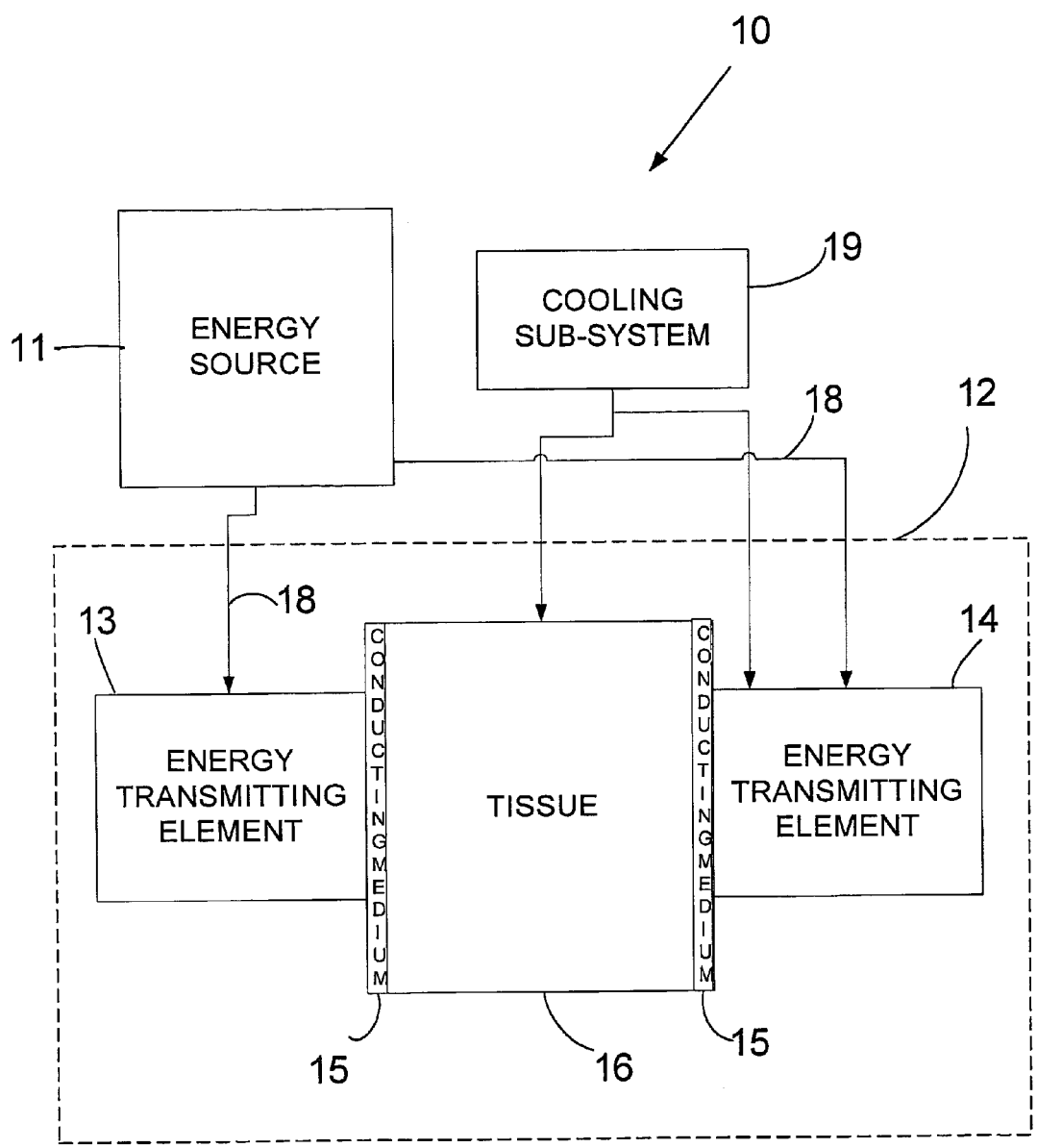
FIG. 2 is a schematic illustration of a system to modify undesirable tissue according to embodiments of the present invention.

Some embodiments of the present invention may enable modifying, treating, destroying and/or removing selected human/animal tissue using an electrical current and/or electromagnetic radiation. For example, such energy may be applied to tissue to heat the undesirable cells to a temperature at which the cells may be modified or destroyed, or to generate required tissue elements. Reference is now made to FIG. 2, which illustrates a system 10 for treating tissue according to some embodiments of the present invention. An energy source 11, for example, an electrical and/or electromagnetic radiation energy source, may provide an electric current and/or electromagnetic radiation to an electrical treatment device 12. The electric current and/or electromagnetic radiation may flow through a conductor 18, for example, wires, fiber optic, air or an alternative conductor to one or more energy transmitting elements 13 and/or 14, for example an electrode, light guide, piezo-ceramic transmitter etc., and/or may flow between energy transmitting elements 13 and 14 through tissue 16. Electric current and/or electromagnetic radiation may enable, for example, heating of target cells to destroy or modify target cells. In other embodiments electric current and/or electromagnetic radiation may be used to provide shock waves or other suitable energy to target cells, to modify or destroy target cells.

According to some embodiments of the present invention, energy source 11 may be an electric current source. In the case where an AC electric current is used, the electric current may first flow to one energy transmitting element, and then the field may reverse and flow to the other energy transmitting element. Current may be pulsed or continuous. Generation of current using frequencies below 100 KHz may result in the current being felt by a patient using electrical treatment device 12. Generation of a current using frequencies above 10 MHz may result in current that may be difficult to control. Generation of current using frequencies between 100 KHz and 10 MHz may be used, according to some embodiments of the present invention, to modify, treat, destroy, and/or remove selected tissue. Other frequencies may be used, including frequencies below 100 KHz and above 10 MHz. The specific heat of adipose tissue may be approximately 3.7 J/cm$^3$/C. If 3.7 Joules of energy is deposited into 1 cubic centimeter of fat, it may raise its temperature approximately 1 degree Celsius (C). To destroy the adipose cell, the cell's temperature may need to be raised approximately 40 degrees C. This requires approximately 150 Joules per cm$^3$, which may be approximately equivalent to depositing 150 watts of energy in one second. Other temperature ranges and energy levels may be used.

In the case where a plurality of energy transmitting elements are used, energy transmitting elements 13 and 14 may be located respectively on at least two sides of a tissue 16, for example, human or animal tissue, thereby conducting electric current through tissue 16. Energy transmitting elements of any suitable shapes and types may be used. For example, when transmitting electric current using an electrode, a second electrode may be used to complete an electric circuit along a preferred path. For example, when using transmitting electromagnetic energy using a transmitting element, a second transmitting element may used to enable extraction of the transmitted energy along a preferred path. Any suitable number of energy transmitting elements may be used, and the energy transmitting elements may be located in any suitable locations. In some embodiments energy transmitting elements that have smooth surface areas and are geometrically shaped (e.g., rounded, squared or rectangular) may be used, to provide a current that is relatively easy to control. Other suitable shapes or energy transmitting element types may be used. Of course, other suitable structures and dimensions may be used.

According to some embodiments of the present invention, energy source 11 may be an electromagnetic radiation source, for example, a light energy source, radio frequency source (RF), ultrasonic energy source or a source of other suitable electromagnetic radiation. Energy transmitting elements 13 and 14 may enable the generation and/or transfer of electromagnetic energy to tissue 16. For example, energy transmitting elements may be electrodes, laser guides, transceivers, or other suitable elements. Suitable energy sources for respective electromagnetic radiation sources may be provided in system 10. According to an embodiment of the present invention, such an energy source may provide, for example, Intense Pulse Light (IPL), laser light, incoherent light, blue light, ultrasonic waves, radio frequency signals, electric current or other suitable energy for treatment of tissue. The electromagnetic radiation may flow through conductors 18, for example, wires, air, fibers, or alternative conductors, to one or more energy transmitting elements, for example, elements 13 and/or 14, and/or may flow between energy transmitting elements 13 and 14 through tissue 16.

According to some embodiments of the present invention, system 10 may include a cooling sub-system 19, to provide cooling for system 10 components and/or tissue 16. For example, cooling sub-system 19 may cool energy transmitting elements 13 and 14, for example to protect the higher resistance stratum cornea, which is a layer of cells on the outermost layer of the epidermis. Cooling sub-system 19 may additionally or alternatively cool the skin on the surface of tissue 16, and/or the upper levels of the tissue etc. A variety of suitable cooling sub-systems may be used, for example, thermal electric cooling mechanisms, water-cooling mechanisms, gas-cooling mechanisms, or other suitable cooling mechanisms. Cooling sub-system 19 may be associated with the skin, energy providing elements, hand piece etc.

According to some embodiments of the present invention system 10 may include a conducting medium or conductive material 15 that may be applied to one or more surfaces of tissue 16, for example, a lotion, gel, liquid suspension, or other suitable conductive material. Conductive material 15 may for example moisten the skin, and use the added moisture to increase the conductivity and decrease the resistance of the surface and/or surface area of the skin. This conductive material may further decrease the friction quotient between the energy transmitting elements and the skin, thereby helping to ease the collecting of tissue between energy transmitting elements. Conductive material 15 may be applied to energy transmitting elements 13 and 14. Various types of conductive material are discussed in detail below.

Figure 3A:
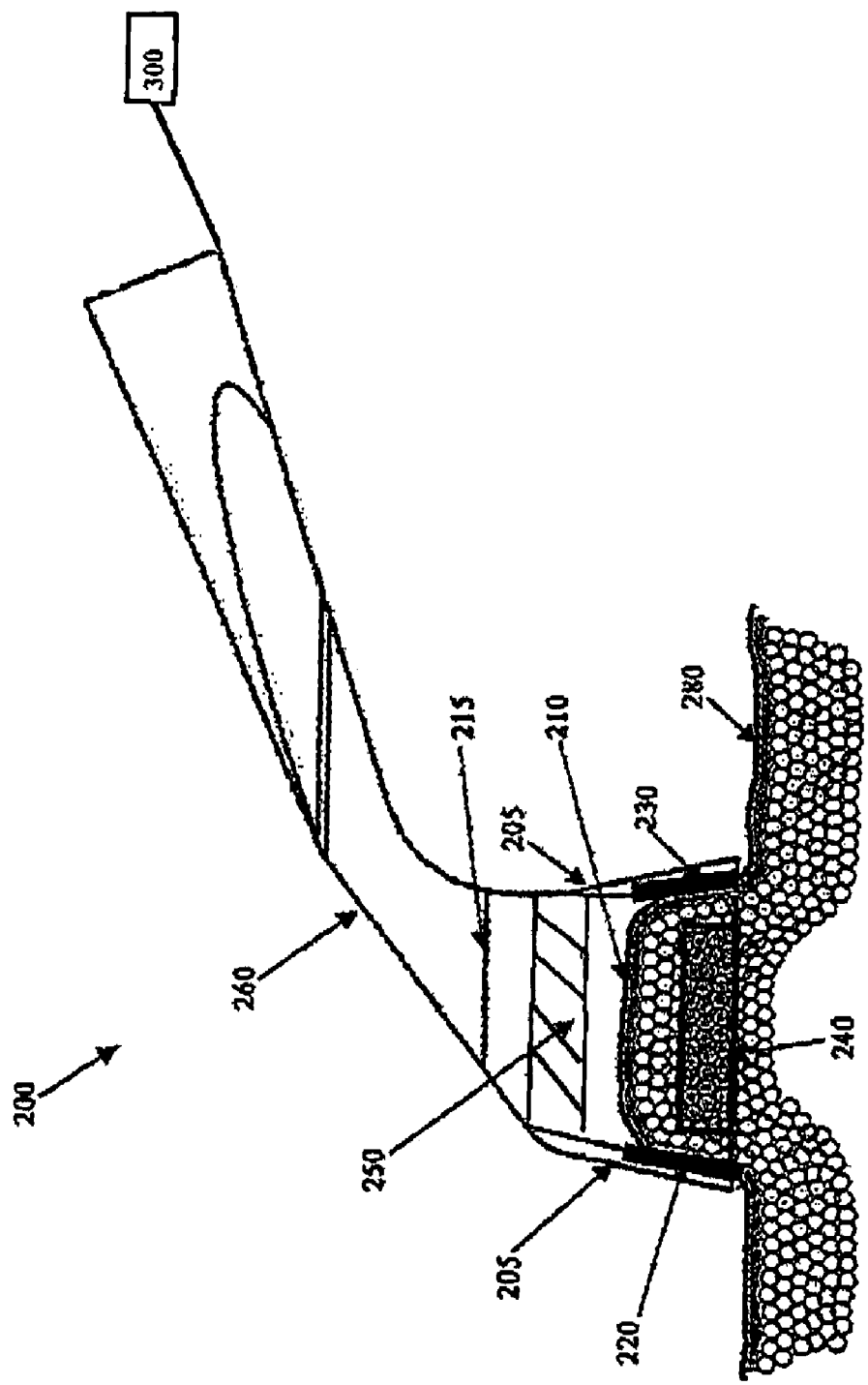
FIGS. 3A–3B are cross section views of the system described in FIG. 2, according to some embodiments of the present invention.

Reference is now made to FIG. 3A, which illustrates an apparatus 200 to enable treatment of selected cells in the dermis or hypodermis layers in the skin. Hand piece 260 may hold or secure the collected, stretched, or pinched skin in place, for example, between energy transmitting elements 220 and 230. For example, hand piece 260 of apparatus 200 may contact the skin 280, and suck up or otherwise secure a section or fold 210 of the skin and underlying tissue 290 into an area 250 of hand piece 260, adjacent to at least one of energy transmitting elements 220 and 230, or between energy transmitting elements 220 and 230. The energy transmitting elements 220 and 230 receive electrical energy, for example, from electrical energy source 300 which is electrically connected thereto. A fold of skin 210 maybe secured, for example, pinched, grabbed, squeezed, nipped, hooked, seized, isolated or otherwise held by pinching arms 205 or tissue holding mechanisms of apparatus 200. Energy transmitting elements 220 and 230 maybe attached or otherwise associated with pinching arms 205. Apparatus 200 may, for example, establish a pathway, for example an electrical pathway, through a secured fold or portion of skin 210 between a plurality of energy transmitting elements, for example, energy transmitting elements 220 and 230.

In one embodiment apparatus 200 may include suction apparatus, which may be used for sucking, pinching, stretching or otherwise maneuvering a fold or portion of skin adjacent to at least one of energy transmitting elements 220 and 230, or between energy transmitting elements 220 and 230. The suction apparatus may include, for example, a piston, an air pump attached via a hose to apparatus 200 etc. By applying suction, the air pressure on the outside of the epidermis may be reduced below the level of the air pressure on the inside of the epidermis. This may force the epidermis and dermis to expand, for example, as a balloon expands when the air pressure inside the balloon increases over the air pressure on the outside. The suction created may pull the skin into a hand piece 260 of apparatus 200, for example, into the area indicated by 250, and between energy transmitting elements 220 and 230. In this way an appropriate amount of skin, which may include a target area 240, may be positioned and/or held in a chosen position for treatment, for example, to secure skin for fat cell removal, hair removal, tattoo removal, scar modifications, and pigmentation modification etc.

In the case where the epidermis and dermis are forced up inside area 250 of hand piece 260, the amount of epidermis and dermis that may enter hand piece 260 may be limited by the dimensions of hand piece 260, the elasticity of the skin, and the friction between the skin and hand piece 260. In one embodiment a material such as a gel, lotion, cream, or other suitable substance may be applied to the skin surface and/or to the surface of the energy transmitting elements, to aid the entering of tissue into hand piece 260. In another embodiment the substance to be applied the skin and/or energy transmitting elements may be electrically conductive. Furthermore, since friction may limit the amount of epidermis and dermis that can be stretched into the hand piece, applying such a lotion, gel, or other suitable substance to the skin may reduce the friction and increase the amount by which the skin stretches.

Once the skin is stretched or pulled into the hand piece, electric current and/or electromagnetic radiation, for example, laser light incoherent light, blue light, electric current, ultrasonic energy, radio frequency (RF) energy etc. may be applied. Since the target area may now be closer to the swface, the electric current and/or electromagnetic radiation may be relatively more effective in removing or modifying the target cells. In one embodiment, as the laser light, for example, enters the skin, it may be scattered in multiple directions. The light that is scattered outward may be reflected back into the treatment zone by a reflective surface 215 located on the sides and/or top of hand-piece 10. Such a surface may recycle the emitted light and further improve the clinical efficacy.

In the case of electromagnetic radiation treatment, the main structure in the epidermis and dermis that absorbs incoming treatment radiation is melanin. The stretching of the epidermis and dermis reduces the density of this melanin, in analogy to an inflating toy balloon. As the balloon inflates, the amount of color dye in the balloon remains constant, the surface area increases, the amount of dye per square centimeter decreases, and the balloon becomes more transparent. The melanin in the skin may function in a similar way to the dye in the balloon. Since its quantity is fixed, as the surface area of the skin increases, the density of melanin decreases, thereby reducing the absorption of the treatment radiation by the skin.

In one embodiment the air pressure in hand piece 260 may be monitored, for example, using an air pressure monitor, to help determine how much tissue has been pulled between hand piece arms 205. In another embodiment an indication as to the amount of tissue held may be determined by, for example, an optical and/or electronic conductive apparatus to determine how much tissue is being held between pinching arms 205. For example, optical sensors may determine the distance between the hand piece aims 205 and tissue 210. For example, electronic detectors may determine the volume of tissue and/or air between the hand piece arms and the tissue. The application of energy to tissue may be controlled according to the results of the pressure monitoring and/or indication. When a preset pressure is reached, for example, the skin may have stretched to a predetermined amount, and hence it may be safe and effective to apply the light.

Figure 3B:
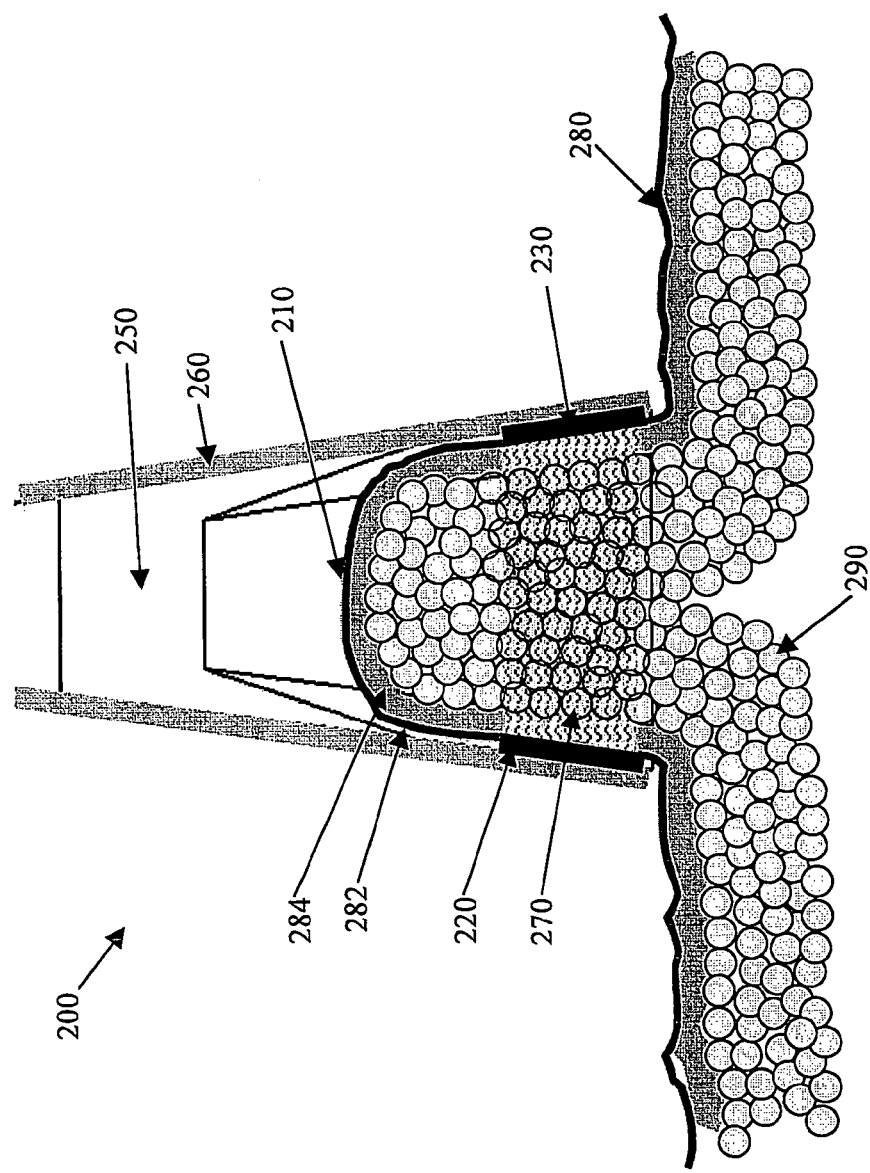

As can be seen with reference to FIG. 3B, in some embodiments of the present invention, when an electrical voltage is applied to energy transmitting elements 220 and/or 230, a current may be conducted through the section of tissue 270, thereby modifying or destroying cells, for example, fat cells within area 270 of skin fold 210. In this example, the current may tend to or prefer to be conducted through the high resistance fat cells 290 because the path length is shorter and the cross-sectional area larger than the path "going around" skin surface 280 from one energy/receiving transmitting element to the other, via the epidermis 282 or dermis 284.

In other embodiments, where electromagnetic radiation is applied to tissue, for example, where ultrasonic energy, RF energy, IPL, laser light, blue light etc. is applied, using energy transmitting elements 220 and 230, cells within area 270 of skin fold 210 may likewise be modified, destroyed etc. According to some embodiments of the present invention, energy transmitting elements 220 and 230 may be or may include, for example, laser guides, electrodes, transceivers or the suitable elements that may enable generation and/or conduction of electromagnetic energy to tissue, for example, fat cells, tattoo ink, lesions, acne bacteria, etc.

According to some embodiments of the present invention the electrical conductivity and/or electromagnetic conductivity of the epidermis may be increased or otherwise altered by applying an electrical and/or electromagnetic conducting medium 15 (e.g., as shown in FIG. 1), for example, a liquid suspension, lotion, gel, liquid, cream, or other suitable material to the surface of tissue 16. This addition to the skin surface may create, for example, a treatment zone that is more conducive of electric current than the naked skin, and may enable greater control over the effect of an electric current and/or electromagnetic radiation on the skin. Application of an electrical conducting medium and/or electromagnetic conducting medium to the epidermis may help control the variability of the epidermis's electrical resistance, for example, by reducing the epidermis's electrical resistance. According to some embodiments such an application may be desirable to reduce the electrical resistance and/or electromagnetic resistance of the epidermis, for example, to avoid excessive heating. Decreasing the electrical resistance and/ar electromagnetic resistance of the outer layers of the epidermis, for example, may result in a more focused absorption of electrical and/or electromagnetic energy into the target cells (e.g., area 240 of FIG. 3A), and correspondingly less peripheral damage to the epidermis.

Conducting mediums such as lotion, gels, and creams etc. may be used in medical procedures to improve the interface between treatment devices and treatment zones. For example ultrasonic gel may be used to provide an impedance match between an ultrasound transducer and a subject's epidermis. Cooling gel may be used for treatments involving light sources such as lasers and intensive pulse light sources. Electrically conducting gel may be used between the energy transmitting elements and the epidermis. According to an embodiment of the present invention, various conducting or other suitable lotions or gels may be applied in such a manner that the lotion or gel may penetrate into the epidermis and for example provide enhanced conduction throughout the epidermis, in addition to the skin surface.

Figure 4A:
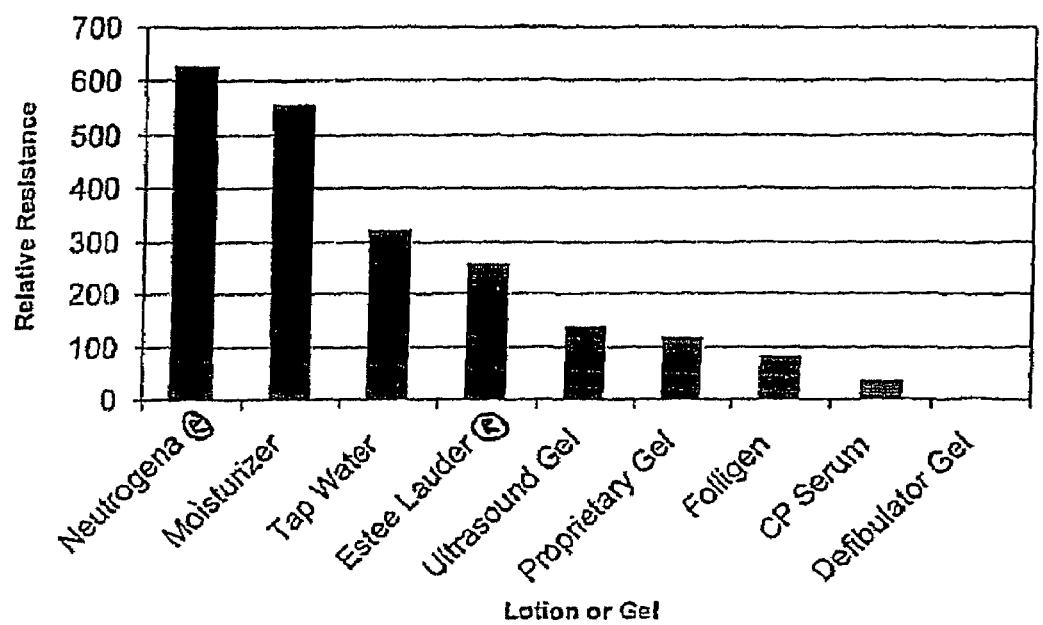
FIGS. 4A–4B are charts illustrating the usage of various examples of gels or lotions, according to an embodiment of the present invention.

According to aspects of the invention, various electrical and/or electromagnetic conducting mediums may be used. The utility of a given conducting medium may be tested in various ways. For example, a voltage may be applied across a small volume of a lotion, and the voltage and corresponding current through the lotion measured. The electrical resistance of the lotion volume may for example be given by the ratio of current to voltage according to Ohm's Law: R V/I. FIG. 4A shows the results of such a test, listing the relative resistances of a plurality of commercial and non-commercial lotions and gels. Other suitable lotions, gels, creams, suspensions etc. may be used Lotions or gels may also be tested by direct application to the epidermis, followed by a determination of the electrical and/or electromagnetic conductivity of the treated area of skin. For example, the conductivity of the untreated skin in the area of the treatment zone may be measured. Lotions or gels may be applied to the area to be treated, and the conductivity may be measured again. Additionally or alternatively, an ultrasound device may be used for a predetermined period of time, to enhance the penetration of the applied lotion or gel. At a selected time period, the electrical resistance may be re-measured. The results of electric conductivity tests for various exemplary lotions, with and without ultrasound enhancement, are shown in FIG. 4B; such results are given by way of examples only, and other suitable lotions or substances with other properties may be used.

Figure 4B:
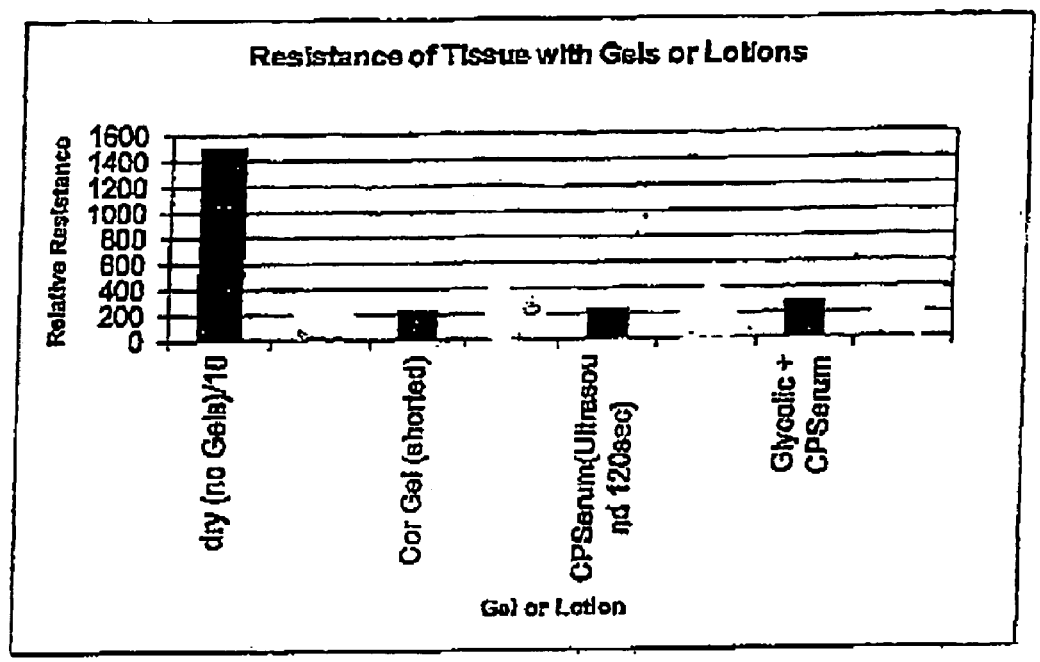

As shown in FIGS. 4A and 4B, a conducting lotion containing copper peptides (CP) may be highly effective in lowering the resistance of tissue. The copper in such a lotion may provide an excellent conductor, and those skilled in the art will recognize that such lotions are already used to generate new collagen in human tissue. Copper peptide lotions may therefore be used to increase the electrical conductivity of the epidermis and/or to help generate new collagen. Other lotions that may be used may include, for example, Vitamin C, retinal acid, Vitamin A, and other suitable elements. According to one embodiment of the present invention an ultrasound device may be used to enhance the penetration of the electrically conducting medium.

Figure 5:
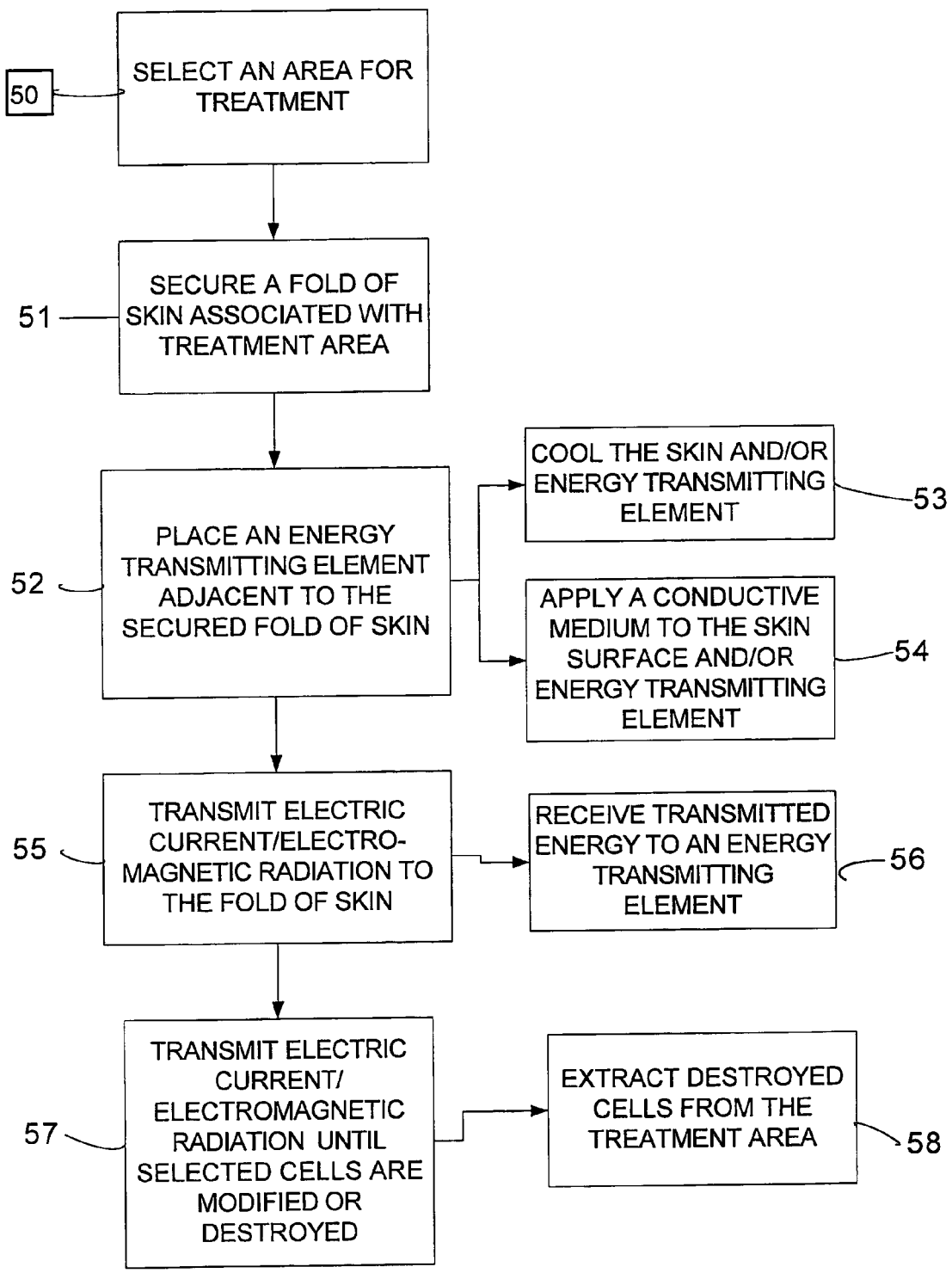
FIG. 5 is a is a flowchart illustrating a method of treating undesirable tissue, according to some embodiments of the present invention.

Reference is now made to FIG. 5, which is a flow chart illustrating a method to modify or destroy undesirable tissue, according to some embodiments of the present invention. At block 50 an area of tissue may be selected for treatment. At block 51 the selected area of skin may be secured, for example, a fold of skin may be sucked, pinched, stretched, or otherwise held by a suction apparatus, a hand etc. The fold of skin may include the epidermis, dermis, and/or hypodermis, any of which may include the target tissue, for example, an adipose layer, degraded protein layer, tumor, lesion etc. In some embodiments the air pressure in a suction apparatus or alternative skin holding device may be measured. In other embodiments optic or electronic mechanisms may be used to determine the volume of skin held by a suction apparatus or alternative skin holding device. The results of such pressure and/or volume determinations may be used to determine how much energy is to be transmitted to the target tissue.

At block 52 one or more energy transmission/reception elements may be placed adjacent to the collected area of skin.

At block 53 selected areas of the tissue may be cooled, for example, to prevent or minimize modification to selected areas. For example, such selected areas may be cooled by cooling the energy transmitting elements, or cooling the skin surface etc.

At block 54 a conducting medium may be applied to selected areas of tissue, for example, to enable the surface or surface area of the tissue to reduce the resistance or increase the conductivity of the epidermis and avoid incidental heating and resultant damage or other undesired modification to the outer layers of the skin, thereby preventing or minimizing modification of these areas due to the applied electric current and/or electromagnetic radiation. An ultrasonic apparatus, for example, may be used to absorb the lotion or gel in the epidermis. The conducting medium may be applied to the energy transmission/reception elements.

At block 55 electric current and/or electromagnetic radiation may be transmitted to the fold of skin, using, for example, treatment device 12. In one embodiment the fold of skin placed between two or more energy transmission elements may enable electricity and/or electromagnetic radiation to be conducted through a path comprising, for example, the epidermis, the dermis, the hypodermis, and then back through the dermis and the epidermis. In other embodiments the path may include the epidermis, the dermis, and may then extend back through the epidermis. Other suitable paths may be affected. In the case where the target tissue is in the hypodermis, the differing heat resistances of the skin layers may result, for example, in approximately 10 times more energy being deposited into adipose tissue elements in the hypodermis, as compared to other tissue elements in the epidermis and dermis. This may enable, for example, heating of adipose or other cells without significant heating of the cells in the epidermis and dermis. According to some embodiments of the present invention, ultrasonic waves, Intense Pulsed Light (IPL), laser pulses, blue light, electric current, and other suitable types of electromagnetic radiation may be transmitted to a target area, thereby modifying fat cells, acne bacteria, tattoo ink collections, or other target cells without significant heating or other modification of the cells in the epidermis and dermis.

At block 56 the electric current and/or electromagnetic radiation may be received by an energy transmission/reception element, thereby providing a preferred path for extraction of transmitted energy from the target tissue.

At block 57 the electric current and/or electromagnetic radiation may be applied, for example, such that the temperature of the target cells (e.g., adipose cells) may reach levels at which the cells are modified or destroyed. For example, the electric current and/or electromagnetic radiation may heat the dermis therefore destroying, for example, degraded collagen and elastin proteins etc., or other elements.

For example, if adipose cells are heated to 60 degrees Celsius (C.) or higher, the cells may be destroyed due to denaturation of the internal proteins. If the adipose cells are heated to 77 degrees C., the cell membrane may dissolve. The cells in the epidermis and dermis may be heated by approximately 4 degree C. or less while the cells in the hypodermis are heated to 40 degrees C. This selectivity may enable destruction of the adipose cells without destroying the cells in the dermis and epidermis. Other suitable temperatures may be used.

Additionally or alternatively, at block 57 the electric current and/or electromagnetic radiation may heat the dermis therefore generating, for example, production of collagen and elastin proteins etc. The epidermis may be cooled during the energy application, and therefore remain substantially unaffected by the application of the electric current and/or electromagnetic radiation. In other embodiments electric current and/or electromagnetic radiation may be used to provide shock waves or other suitable energy to target cells, to modify or destroy cells. In other embodiments similar procedures may be used to enable for example removal of hair, stimulation of hair growth, removal of capillaries, removal of pigmented lesions, removal of tattoos, etc. Other steps or series of steps may be used.

Electromagnetic radiation that may be applied to an area to be treated may include, for example, IPL, laser light, blue light, ultrasonic energy, RF energy, electric current, or other suitable energies, or combinations of energies.

According to some embodiments of the present invention, the lower resistance to electrical energy and/or electromagnetic energy of the target tissue compared to the resistance of surrounding tissues may be used to modify or treat selected targets. Blood, for example, has a lower electrical resistance than its surrounding tissues (blood has the highest conductivity of any entity in the body) for example, being approximately one half to one third the electrical resistance of its surrounding tissue. By using a system, for example, similar to that described above with reference to FIG. 2, electric current applied to a tissue mass may, for example, be substantially conducted by the blood and not by the surrounding tissue. In cases such as port wine stains, rosacea, or telangiectasias, or other skin conditions where there is a plexus of blood vessels near the surface of the skin, an applied electric current may be better conducted by this plexus than by the surrounding issue. This may result, for example, in preferential heating of the small capillaries in the plexus. With sufficient current, for example, the blood may be heated to its coagulating temperature, for example, and may seal off selected blood vessels, for example, those comprising the vascular lesions. By sealing the vessels the dead cells of the plexus may be removed by the body. In some embodiments electromagnetic radiation may be used to heat the blood to its coagulating temperature etc.

At block 58, destroyed cells may be extracted from the treatment area.

Figure 6:
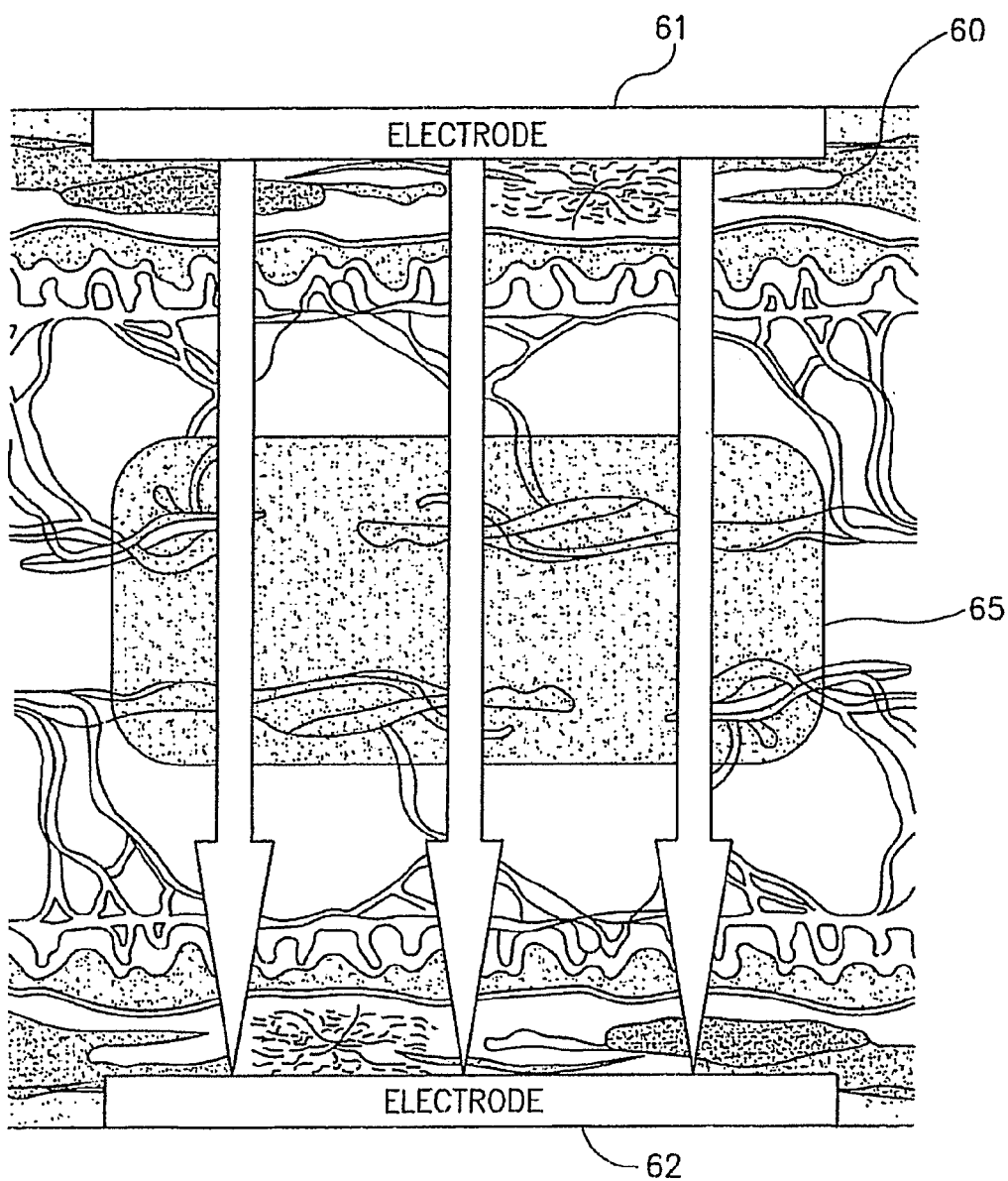
FIG. 6 is a graphical illustration of the effects of implementing the tissue modification method using a system according to an embodiment of the present invention.

Reference is now made to FIG. 6, which illustrates a graphic example of the effects an applied current may have on the epidermis, dermis, and hypodermis layers of selected tissue, using, for example, the system described in FIG. 2, according to an embodiment of the invention. As can be seen in FIG. 6, current applied to a layer of tissue 60 folded between two or more energy transmitting elements, such as electrodes 61 and 62, may travel from, for example, electrode 61, through the cellular structure, the intercellular tissue, and the blood vessels etc., to electrode 62. The current may affect the area of tissue between the electrodes. In some embodiments, for example, where cooling may be applied to the dermis and/or epidermis, the heating resulting from the electric current may not effect or effect relatively little the areas of tissue that are relatively close to the epidermis and/or dermis. In such a case, the heat resulting from the electric current may be concentrated in a region of the tissue that may be relatively far from the epidermis and/or dermis, for example, in area 65. Other areas may be designated for cooling and/or heating.

In other embodiments therapeutic ultrasonic waves, light treatment, laser light, RF, blue light or other suitable electromagnetic radiation may be applied to target tissue within collected skin, using one or more energy transmitting elements. For example, electromagnetic radiation may be applied to target tissue using an energy transmitting element. In some embodiments the energy applied may be received by a second energy transmitting element, to help diffuse the energy in a controlled way, thereby helping prevent undesirable effects of the electromagnetic radiation.

In other embodiments energy may be applied to collected skin, which may be collected, for example, with a suction mechanism. Additionally, the epidermis may be cooled during application of electromagnetic radiation, such that when a hand-piece component pulls the skin into the hand piece, it may be in contact with a cold element. Components of the hand-piece, and/or the skin surface, may be cooled, for example, by circulating cold water, or my other suitable cooling mechanisms. Additionally, a conducting medium may be applied to the skin surface or the energy transmitting elements.

According to one embodiment of the present invention, system 10 may be used for removing and/or treating wrinkles. Wrinkles in human skin may partially result from degradation in the quality and/or quantity of collagen and elastin proteins in the dermis. Heating, for example, the dermis may trigger the generation of new collagen and/or elastin, resulting in the wrinkles being smoothed. Since these proteins reside in the dermis, which lies under the epidermis, it may be desirable that this heating takes place without damaging the epidermis.

According to one embodiment of the present invention, blue light may be applied to target tissue, for example, for removal of P.Acne bacteria. In such an application, the energy transmitting elements 13 and 14 may be made of sapphire or other suitable materials. The energy transmitting elements 13 and 14 may apply blue light, for example, by transmitting blue light for a few seconds. Without the cooling, the blue light would possibly burn the tissue in a few seconds, however with the cooling, the blue light may be used substantially indefinitely. Since the action of the light and the porphorins is photochemical, the reaction may proceed regardless of the temperature, thereby enabling destruction of the P.Acne bacteria in spite of the cooling. In some embodiment the reaction may be slightly slower due to the effect of the cooling.

In one embodiment as shown in FIG. 3A, the suction may pull the targeted bacteria and sebaceous gland closer to the surface so that less light from the optical source in area 250 is applied to the skin 210 required for the treatment. In some embodiments scars may be treated or removed by the application of blue light and the usage of cooling elements. For example, to enable scar treatment/removal, the blue light output may be changed from the blue portion of the light speclrwn to, for example, the ultraviolet B (UVB) and ultraviolet A (UVA) portion. A similar hand-piece such as a band piece component with a cooling element may be used.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. Apparatus comprising:
  a device having a cavity therein, said cavity having at least two electrodes having contact surfaces adapted to contact tissue collected therebetween, and said cavity further having a suction lumen in communication therewith;
  an optical energy source adapted for transmitting optical energy to an outer surface of said tissue collected between said electrodes; and
  an electrical energy somce connected to said electrodes.

2. The apparatus of claim 1, wherein said electrical energy is radio frequency (RE) energy.

3. The apparatus of claim 2, further comprising a suction mechanism in communication with said suction lumen.

4. The apparatus of claim 3, wherein said optical energy is selected from the group consisting of Intense Pulsed Light, laser energy, and blue light.

5. The apparatus of claim 4, comprising a reflector in said cavity for reflecting optical energy scattered from said outer surface of said tissue back thereto.

6. The apparatus of claim 2, comprising a cooling mechanism for cooling an outer surface of said tissue collected between said electrodes.

7. A method for treating skin tissue, the method comprising:
   collecting a portion of skin tissue between at least two contact surfaces of respective at least two electrodes, such that an outer surface of said tissue is in contact with said surfaces of said electrodes;
   transmitting optical energy from an optical energy transmitting element to a first partion of skin tissue collected between said electrodes for treating said portion; and
   applying electrical energy to a second portion of tissue collected between said electrodes for treating the skin tissue.

8. The method of claim 7, wherein said electrical energy is radio frequency (RF) energy.

9. The method of claim 8, wherein said collecting a portion of tissue comprises applying negative pressure to said portion of tissue.

10. The method of claim 8, comprising applying an electromagnetic conductive medium to said portion of tissue.

11. The method of claim 10, wherein said electromagnetic conductive medium is a conductive lotion.

12. The method of claim 8, comprising measuring the volume of said collected portion of tissue.

13. The method of claim 8, wherein said optical energy is selected from the group consisting of intense Pulsed Light laser energy, and blue light.

14. The method of claim 8, comprising reflecting optical energy scattered from said outer surface of portion of tissue back thereto.

15. The method of claim 8, comprising cooling an outer surface of said portion of tissue.

16. The method of claim 7, further comprising applying a lotion between said electrode surfaces and said portion of tissue.

17. The method of claim 7, further comprising applying a gel between said electrode surfaces and said portion of tissue.

18. The method of claim 7, wherein said first portion and said second portion are substantially the same portion.

* * * * *